(12) United States Patent
Leclerc

(10) Patent No.: US 8,691,524 B2
(45) Date of Patent: *Apr. 8, 2014

(54) METHOD FOR ISOLATING A PART OF A LAYER OF A BIOLOGICAL MATERIAL

(75) Inventor: Norbert Leclerc, Jena (DE)

(73) Assignee: Molecular Machines & Industries AG, Glattbrugg (CH)

( * ) Notice: Subject to any disclaimer, the term of this patent is extended or adjusted under 35 U.S.C. 154(b) by 290 days.

This patent is subject to a terminal disclaimer.

(21) Appl. No.: 13/024,121

(22) Filed: Feb. 9, 2011

(65) Prior Publication Data

US 2011/0192534 A1 Aug. 11, 2011

Related U.S. Application Data

(63) Continuation of application No. 10/202,118, filed on Jul. 24, 2002, now Pat. No. 8,535,905, which is a continuation of application No. PCT/EP01/00802, filed on Jan. 25, 2001.

(30) Foreign Application Priority Data

Jan. 25, 2000 (DE) .................................. 100 03 588

(51) Int. Cl.
*A61B 18/20* (2006.01)

(52) U.S. Cl.
USPC ................... 435/40.52; 435/40.5; 435/288.1; 435/288.3; 422/916; 606/1; 606/10

(58) Field of Classification Search
USPC .......... 606/1, 3, 10–14; 422/916; 435/4–7.21, 435/7.23, 30, 40.5, 40.51, 40.52, 63, 64, 435/164, 283.1, 287.1, 287.3, 287.7, 287.8, 435/287.9, 288.1, 288.3, 304.3
See application file for complete search history.

(56) References Cited

U.S. PATENT DOCUMENTS

| | | |
|---|---|---|
| 4,624,915 A | 11/1986 | Schindler et al. |
| 5,859,699 A | 1/1999 | Baer et al. |
| 5,985,085 A | 11/1999 | Baer et al. |
| 5,998,129 A | 12/1999 | Schuetze et al. |
| 6,528,248 B2 | 3/2003 | Lossing et al. |

*Primary Examiner* — David Shay
(74) *Attorney, Agent, or Firm* — Henry M. Feiereisen LLC; Ursula B. Day

(57) ABSTRACT

A film (14) with a tissue section (10) is placed with the tissue section (10) downward on a microscope slide (18) and the microscope slide (18) positioned in the object plane of an inverse microscope; where an adhesive tape (20) is arranged, with a bonding agent (22) downward, above the film (14) and therefore above the tissue section (10); wherein the next step, tissue (36) to be isolated is excised by a focused laser beam, which also divides the film (14); whereupon removal of the adhesive tape (20) from the microscope, the excised tissue pieces (36) adhere to the adhesive tape (20), and the remnant of the film (14) and of the tissue section (10) remains adhering to the microscope slide (18).

6 Claims, 4 Drawing Sheets

METHOD FOR ISOLATING A PART OF A LAYER OF A BIOLOGICAL MATERIAL

CROSS-REFERENCES TO RELATED APPLICATIONS

This application is a continuation of prior filed U.S. application Ser. No. 10/202,118, filed Jul. 24, 2002, now U.S. Pat. No. 8,535,905, the priority of which is hereby claimed under 35 U.S.C. §120, and which in turn is a continuation of PCT International Application Number PCT/EP01/00802, filed Jan. 25, 2001, which designated the United States and has been published as International Publication Number WO 2001/055693, and on which priority is claimed under 35 U.S.C. §120, and which claims the priority of German Patent Application No. 100 03 588.4, filed Jan. 25, 2000, pursuant to 35 U.S.C. 119(a)-(d).

BACKGROUND OF THE INVENTION

The present invention relates to a method for isolating a part of a layer of biological material.

FIELD OF THE INVENTION

In order to discover the molecular causes of diseases, so-called gene expression studies are carried out. They involve trying to determine the genes that are actually expressed in a cell, since the associated proteins are responsible for the pathological development of cells. One way of determining which proteins are actually present is to determine the mRNA that is synthesized in the cell, since the proteins are formed from it.

However, mRNA is a very short-lived product of cells, so that the concentration of mRNA in cells is very low. If it is desired to determine the mRNA, for example of a tumor cell, then it is necessary to collect as a large a number of tumor cells as possible. To that end, the tumor cells need to be isolated from the diseased tissue. To do this, for example, the tumor cells may be excised from tissue sections and collected in isolation. The isolated tumor cells are subsequently broken up. Through suitable purification steps, the mRNA is isolated from the cells. It is then transcribed into cDNA by means of reverse transcriptase. This is done, as a rule, using linear PCR. The cDNA obtained in this way is qualitatively or quantitatively analyzed with the aid of suitable DNA chips.

In this context, the present invention concerns the isolation, or extraction, of cells to be studied. One of the important aspects of this is to work extremely cleanly, that is to say in particular free from RNAses, since they degrade mRNA. Even contact with the bare hand is to be avoided.

In known methods for cutting tissue (for example the American Journal of Pathology, Vol. 151 (1997), pages 63-67), the tissue section is prepared on a slide. With the aid of a laser, a closed curve is described around the diseased tissue. The tissue is ablated on the curve, so that the diseased tissue to be isolated is separated from the remaining tissue. The excised tissue piece can be taken up, for example, with the aid of a pipette. A disadvantage with the known method is that it is very time-consuming. In order to collect the amount of mRNA needed for one analysis, a person is occupied with cutting tissue for several days.

An improved method as described in DE 196 16 216 A1 (see also Cell. Mol. Bio., Vol. 44 (1998) pages 735-746). A tissue section prepared on a slide is placed on an inverse or upright microscope. A seal element of a sealable tube is arranged above the tissue section on the slide. The bottom or inner side of the seal element is coated with oil. Ablation by a UV laser is used to excise parts of the tissue on the slide. The excised parts of the tissue are detached from the slide by means of a UV light pulse. When this happens, they strike the oil-coated seal element and adhere to the oil. This obviates time-consuming take-up with a pipette. A disadvantage, however, is the poorly controllable movement of the detached tissue piece. It does not always reach the seal element. Furthermore, the UV light pulse damages precisely the same tissue as needs to be studied.

SUMMARY OF THE INVENTION

It would therefore be desirable and advantageous to provide an improved method to obviate prior art shortcomings and to provide a method, and an associated retaining part, with the aid of which larger amounts of tissue can be collected in as sterile a way as possible and rapidly.

The present invention resolves prior art problems by a method for isolating a part of a layer of biological material, comprising the steps of
  applying the layer of biological material to one side of a stabilization layer;
  forming a substrate with a bonding layer on at least one side of the substrate, and wherein the material of the bonding layer is a material suitable for promoting adhesion between the stabilization layer and the substrate;
  bringing the substrate with its bonding layer into contact with the stabilization layer on the side of the stabilization layer away from the layer of biological material;
  focusing a laser beam and describing one of a closed or substantially closed curve around the part of the layer of biological material to be isolated where it erodes the biological material and the stabilization layer on the curve; and
  then separating the substrate and those parts of the stabilization layer which are not in contact with the part of the layer of biological material to be isolated.

According to one aspect of the present invention for isolating a part of a layer of biological material, the layer of biological material is first applied to one side of a stabilization layer. A substrate is formed with a bonding layer on at least one side of the substrate. In this case, the material of the bonding layer is selected in such a way that it can promote adhesion between the stabilization layer and the substrate. The substrate is subsequently brought, with its bonding layer, into contact with the stabilization layer on the other side of the stabilization layer from the layer of biological material. The focus of a laser beam then describes a closed curve around the part of the layer of biological material to be isolated, and it erodes the biological material as well as the stabilization layer on the curve. By means of this, the part to be isolated is separated from the remnant of the layer of biological material. The substrate and those parts of the stabilization layer which are not in contact with the part of the layer of biological material to be isolated are subsequently separated. The isolated part adheres to the substrate.

As an alternative, the part to be isolated may first be separated from the remnant of the layer. Only then is the substrate brought, with its bonding layer, into contact with the stabilization layer on the other side of the stabilization layer from the layer of biological material. Then, once again, the substrate and those parts of the stabilization layer which are not in contact with the part of the layer of biological material to be isolated are subsequently separated. The isolated part once again adheres to the substrate.

Furthermore, the focus of the laser beam does not need to describe a completely closed curve around the part of the layer of biological material to be isolated. It is sufficient for an approximately closed curve to be described. One or more bridges on which the part to be isolated is retained, for example, may be left standing between the part to be isolated and the remnant. When separating the substrate and the parts that are not to be isolated, the bridges will be severed and the parts to be isolated will be disconnected. They then once more adhere to the substrate, as desired.

The layer of biological material may, for example, be a tissue section, a cell smear or seeded cells.

Films, for example, may be used for the stabilization layer. After the method according to the invention has been carried out, the part of the section to be isolated, for example tumor cells, adheres to the substrate, while the remnant of the section, for example healthy tissue, continues to adhere to the remaining stabilization layer. The part of the section to be isolated is hence isolated.

In another aspect of the invention the method provided comprises the steps of:
  applying the layer of biological material to one side of a stabilization layer;
  the stabilization layer with the layer of biological material is positioned suspended above a catching device, wherein a gap is left between the stabilization layer and the catching device;
  then the focus of a laser beam describes a closed curve around the part of the layer of biological material to be isolated, and it erodes the biological material as well as the stabilization layer on the curve, so that the part to be isolated is separated from the remnant of the layer of biological material; and
  then the part to be isolated falls onto the catching device and is caught by it.

In the method according to the invention, the layer of biological material is first applied to one side of a stabilization layer. The stabilization layer is positioned with the layer of biological material suspended above a catching device, a gap being left between the stabilization layer and the catching device. The focus of a laser beam subsequently describes a closed curve around the part of the layer of biological material to be isolated, and it erodes the biological material as well as the stabilization layer on the curve. By means of this, the part to be isolated is separated from the remnant of the layer of biological material. The part of the biological material to be isolated, for example the tumor cells, falls directly onto the catching device, and it can thus be easily isolated and, for example, transported further.

The gap between the stabilization layer and the catching device may, for example, be an air gap, although it may also be filled with a suitable gas or have a reduced pressure applied to it.

The gap between the stabilization layer and the catching device may be produced in a straightforward way by using a slide with an indentation as the catching device and by positioning the part to be isolated above the indentation in the slide.

As an alternative, the gap between the stabilization layer and the catching device may be produced by arranging spacers between the stabilization layer and the catching device.

As a rule, tissue samples are first cut in thin wafers, then applied to a slide and optionally dyed, subsequently provided with a transparent mounting medium (alcohol, xylene) and finally covered with a cover glass. A tissue section prepared in such a way can be observed with a good imaging quality under a microscope. If it is desired to excise individual sections or cells from the tissue (micro dissection) and to process them further in some other way, then it is not necessary to use a mounting medium and a cover glass. The consequence of this is a dramatic deterioration of the imaging quality in the microscope, since the light is then strongly refracted and scattered because of large differences of refractive index between the sample, air and the optical system, and because of the rough surface of the sample.

A light diffuser, for example a scattering screen, a matt screen or matt glass, may be arranged between the illuminating instrument and the sample. It has been shown that this leads to a substantial improvement of the imaging quality, so that the image when using a light diffuser has a quality still approaching that when a mounting medium and a cover glass are used.

To that end, it is possible to provide a retaining part with a flat bottom, which acts as a light diffuser. An edge rises above the bottom. A handling device, which is directed outward away from the bottom, adjoins the other side of the edge from the bottom.

The retaining device may, for example, be a simple handle or a connection to a sealable tube.

The retaining part can hence both collect the isolated tissue parts and also act as a light diffuser, and it can be manipulated easily by means of the handling device.

Advantageously, the light diffuser is arranged at most 2 mm away from the layer of biological material. The bottom of the seal element therefore has a thickness of at most 2 mm in the vicinity of the light diffuser.

If the retaining part is brought up to the layer of biological material from below, then the edge should project by between 0.1 and 2 mm beyond the bottom on the other side from the handling device. In this way, the required gap is set up automatically. Such a design of the bottom of the retaining part, however, cannot be used if the bottom needs to be brought directly into contact with the layer of biological material or the stabilization layer.

In order to catch or collect the isolated parts of the layer of biological material, the bottom of the retaining part is provided with a bonding layer on the other side from the handling device.

In a refinement of the invention, the retaining part is connected integrally via a flexible connecting strip to a sealable tube, for which it serves as a seal element. By tilting with the flexible connecting strip, the tube can be sealed. After the tissue has been caught, or collected, the seal element can be simply folded shut. The isolated tissue section is enclosed in the sterile tube.

Such a tube can straightforwardly be tilted under the sample or tilted out of the light and/or the manipulation path. In this way, the tissue section can furthermore be reached for different manipulations, for example taking the sample mechanically.

The retaining part may be used as a catching device or as a substrate for collecting the isolated tissue parts.

With the method according to the invention, it is even possible to isolate very small, sometimes individual, tumor cells in a tissue section in a common working step, and to collect them with a common catching device.

Further advantageous refinements of the method according to the invention are in accordance with the dependent claims.

BRIEF DESCRIPTION OF THE DRAWING

Other features and advantages of the present invention will be more readily apparent upon reading the following description of currently preferred exemplified embodiments of the invention with reference to the accompanying drawing (which are not true to scale), in which.

DETAILED DESCRIPTION OF PREFERRED EMBODIMENTS

Figure 1A:
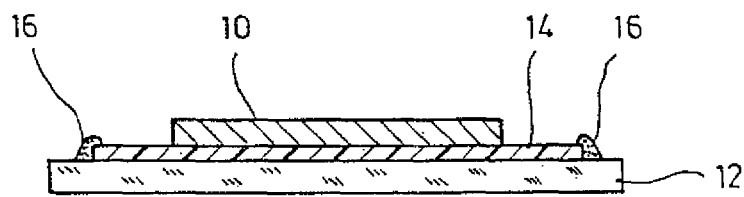
FIG. 1A-1D are schematic representations of a method for isolating a part of a layer of biological material.

Throughout all the Figures, same or corresponding elements are generally indicated by same reference numerals.

Turning now to the drawing, and in particular to FIG. 1, there is shown a

Reference will be made below to FIG. 1A).

Tissue which is frozen or embedded in paraffin is broken down into thin tissue sections 10 with a planing blade. As a rule, these roll up.

A microscope slide 12 is sprayed with alcohol. A piece of a film 14, which measures a few square centimeters in size and is backed by a paper layer, is placed on the face of the microscope slide 12 that has been sprayed with alcohol. This film 14 consists, for example, of a 2 µm thickness of UV-absorbing PET or PEN. The paper is subsequently removed. The film 14 is then fixed at its edge to the microscope slide 12 by an adhesive 16, for example a mounting adhesive.

The rolled-up tissue section 10 is then placed onto the film 14. The microscope slide 12 with the film 14 and the tissue section 10 is heated to 60° Celsius, so that the paraffin melts and the tissue section 10 unrolls.

Figure 1B:
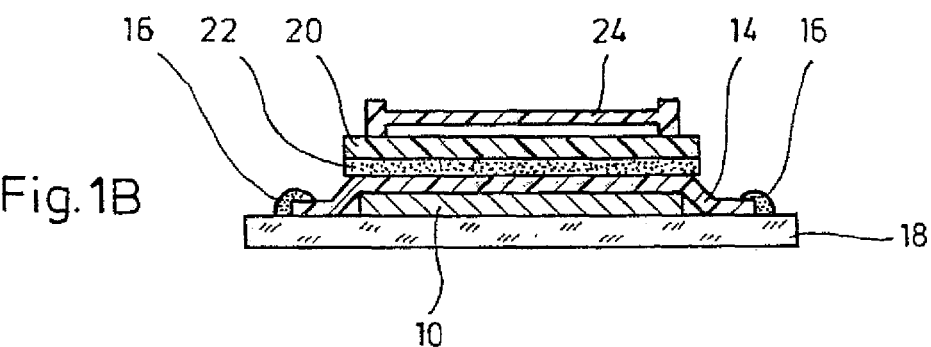

Method 1:

Reference will be made below to FIG. 1B). In the currently preferred exemplary embodiment, the film 14 with the tissue section 10 is subsequently taken from the microscope slide 12 and is placed, with the tissue section 10 downward, onto a second microscope slide 18. On this second microscope slide 18, the film 14 is once again fixed at its edge by an adhesive 16. The second microscope slide 18 is then placed into the objective plane of an inverse microscope.

In one exemplary embodiment, an adhesive tape 20 with a bonding agent 22 arranged on the bottom may be positioned on the film 14, and therefore above the tissue section 10. Instead of the adhesive tape 20, 22, it is also possible to use different bonding films, for instance those from the semiconductor industry which, for example, use silicone resin as the bonding agent 22. A light diffuser 24 is placed on the adhesive tape 20. The tissue is subsequently illuminated from above by an illuminating instrument. It is also possible for the adhesive tape 20 itself to act as a light diffuser.

Figure 1C:
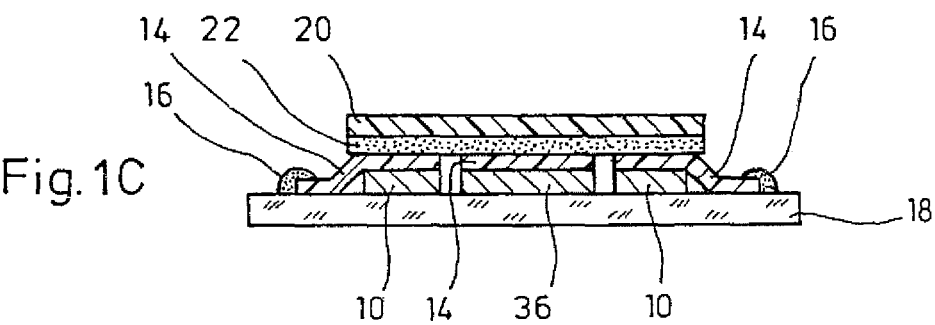

Reference will be made below to FIG. 1C). The tissue 36 to be isolated is subsequently excised in the inverse microscope by the focused beam, for example of a nitrogen laser with a wavelength of 337 nm and a power density of about $10^8$ to $10^9$ W/cm$^2$. This also divides the UV-absorbing film 14. The light diffuser is then removed.

Figure 1D:
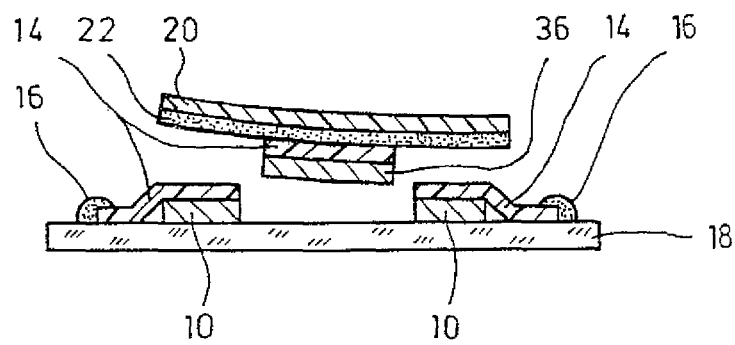

Reference will be made below to FIG. 1D). The adhesive tape 20 is then removed from the microscope. When this happens, the excised tissue pieces 36 adhere to the adhesive tape 20. The remnant of the film 14 and of the tissue section 10 is fixed by the adhesive 16 to the second microscope slide 18, and remains adhering to it.

Figure 2A:
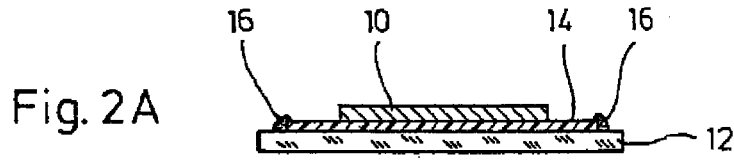
FIG. 2A-2E are schematic representations of an alternative method for isolating a part of a layer of biological material.
Figure 2B:
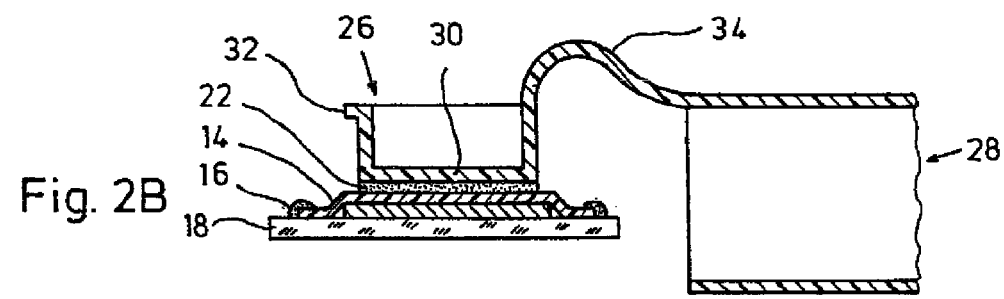

Reference will be made below to FIG. 2A) and FIG. 2B). In the currently preferred exemplary embodiment, however, the seal element 26 of a sealable plastic tube 28 has a bonding agent 22, for example silicone resin, applied to one side of it. For this purpose, that side of the seal element 26 is selected which is in contact with the interior of the tube, when the tube is sealed by the seal element.

This seal element 26 has a flat bottom 30, which consists of a light-scattering material. Above the bottom 30, a circumferential edge 32 rises. The edge 32 is connected integrally to the tube 28 via a flexible connecting strip 34. By tilting the seal element 26 with the flexible strip 34, the tube 28 can be sealed. The seal element 26 is arranged, with the bonding agent 22 downward, above the film 14 and therefore above the tissue section 10. The tissue section 10 is illuminated from above by an illuminating instrument, through the light-scattering seal element 26.

Figure 2C:
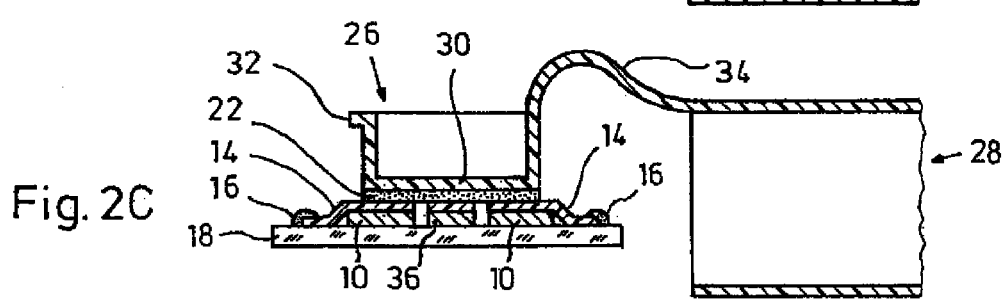

Reference will be made below to FIG. 2C). The tissue 36 to be isolated is subsequently excised in the inverse microscope by the focused beam, for example of a nitrogen laser with a wavelength of 337 nm and a power density of about $10^8$ to $10^9$ W/cm$^2$. This also divides the UV-absorbing film 14.

Figure 2D:
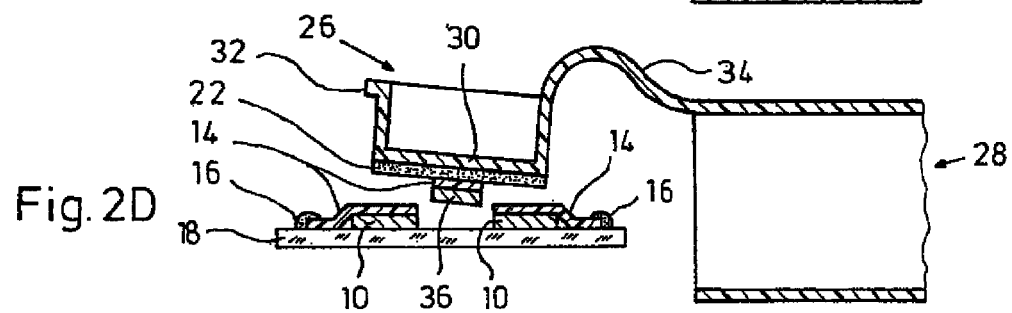

Reference will be made below to FIG. 2D). The seal element 26 is then removed from the microscope. When this happens, the excised tissue pieces 36 adhere to the bottom 30 of the seal element 26. The remnant of the stabilization layer 14 and of the tissue section 16 is fixed by the adhesive 16 to the second microscope slide 18, and remains adhering to it.

Figure 2E:
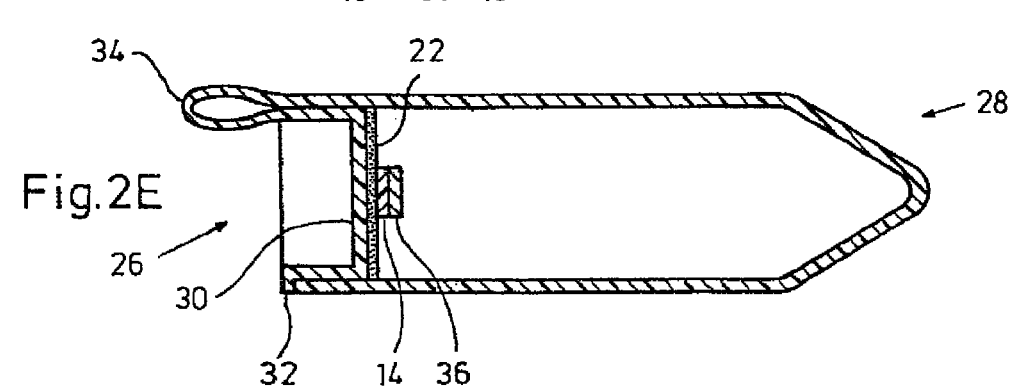

Reference will be made below to FIG. 2E). The plastic tube 28 is sealed by the seal element 26. The excised tissue piece 36 is therefore situated in the sterile space of the tube 28. It has therefore been isolated in a highly pure way.

Figure 3A:
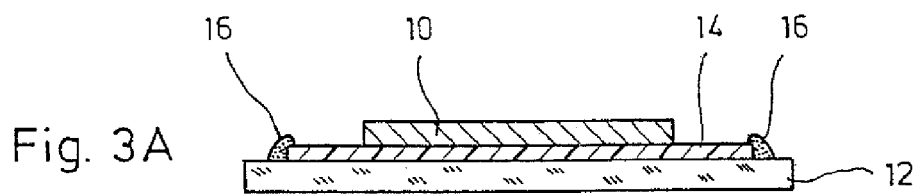
FIG. 3A-3E are schematic representations of a further alternative method for isolating a part of a layer of biological material.

Method 2:

Reference will be made below to FIG. 3A) and FIG. 3B). In an alternative method, the film 14 with the tissue section 10 is taken from the microscope slide 12 and placed, with the tissue section 10 downward or upward, onto a second microscope slide 18. In this case, spacers 38 with a height of about 0.1 mm are arranged on the second microscope slide. An air gap 40 is thereby created under the film 14 with the tissue section 10.

Figures 3B, 3C:
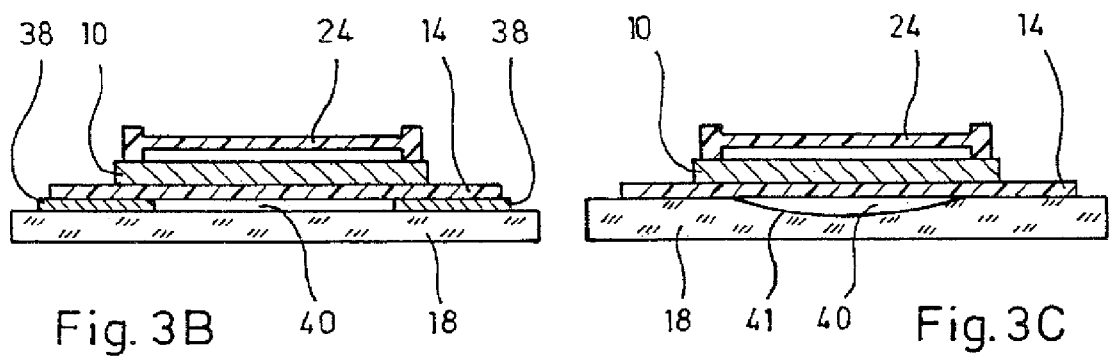

Reference will be made below to FIG. 3C). As an alternative, the gap 40 between the film 14 and the second slide 18 may also be produced by a concave indentation 41 in the second slide 18, instead of by spacers 38.

The second slide 18 prepared in such a way is brought into the object plane of an inverse microscope. The diffuser 24 is introduced into the illumination path of the inverse microscope extending above. It is positioned about 0.1 to 0.2 mm above the sample 10.

Figure 3D:
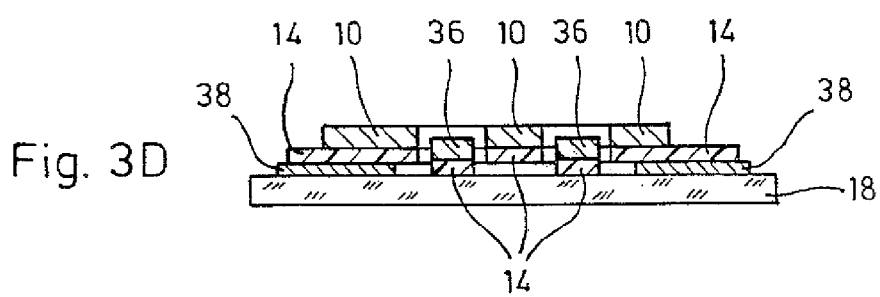
Figure 3E:
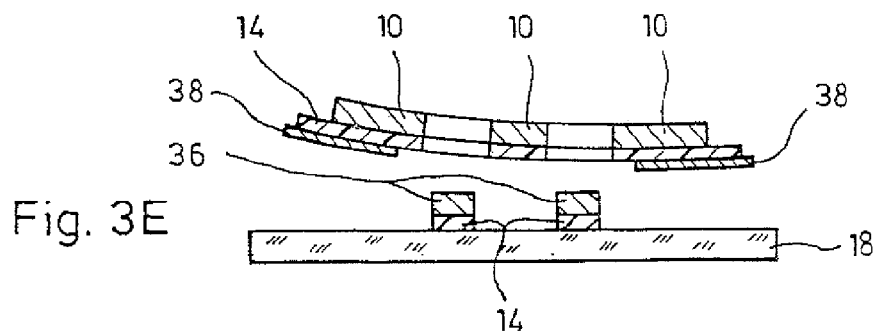

Reference will be made below to FIG. 3D). The tissue 36 to be isolated is subsequently excised by a focused UV laser beam. This also divides the UV-absorbing film 14. The part 36 of the biological material to be isolated therefore falls onto the second slide 18, so that it can be transported further in a straightforward way (see FIG. 3E).

Figure 4A:
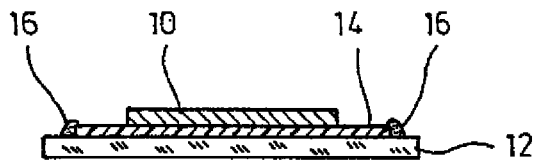
FIG. 4A-4D are schematic representations of a further alternative method for isolating a part of a layer of biological material.
Figure 4B:
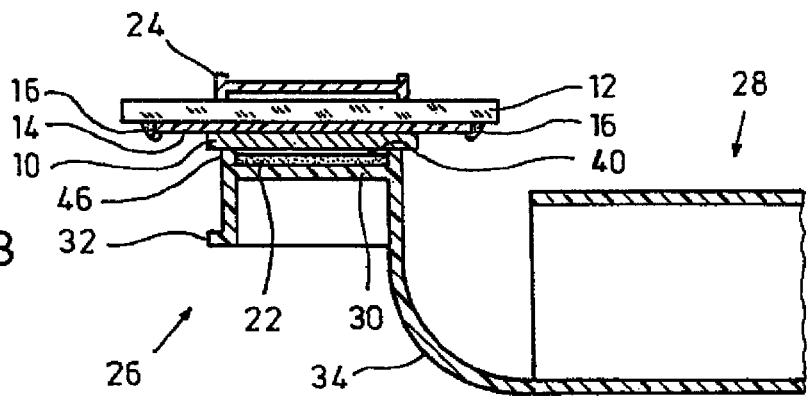

Method 3:

Reference will be made below to FIG. 4A) and FIG. 4B). In a further alternative method, the microscope slide 12, with the film 14 and the tissue section 10 downward, is brought into the object plane of an upright microscope.

In this exemplary embodiment, the seal element 26 of a sealable plastic tube 28 has a bonding agent 22, for example silicone resin, applied to it. The seal element 26 of the tube 28 is positioned underneath the sample 10. The seal element 26 has a flat bottom 30. On the same side of the seal element 26 as the sample 10, a circumferential edge 46 rises about 0.1 to 2 mm above the bottom 30. A further edge 32 rises on the opposite side of the bottom 30. This second edge 32 is connected integrally to the tube 28 via a flexible connecting strip 34. By tilting the seal element 26 with the flexible connecting strip 34, the tube 28 can be sealed.

The seal element 26 is positioned, with the bonding agent 22 downward, under the sample 10. The tissue 10 is illuminated from below by an illuminating instrument, through the seal element 26 that acts as a light diffuser.

Figure 4C:
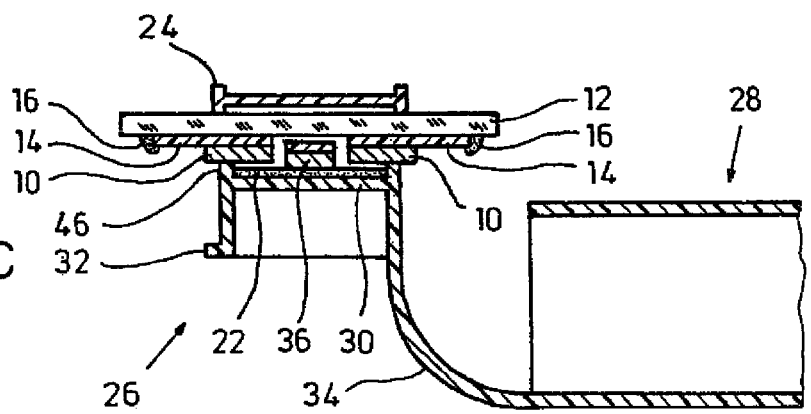

Reference will be made below to FIG. 4C. The tissue 36 to be isolated is once again excised by the focused beam, for example of a nitrogen laser with a wavelength of 337 nm and a power density of about $10^8$ to $10^9$ W/cm$^2$, which is incident from above. This also divides the UV-absorbing film 14.

Figure 4D:
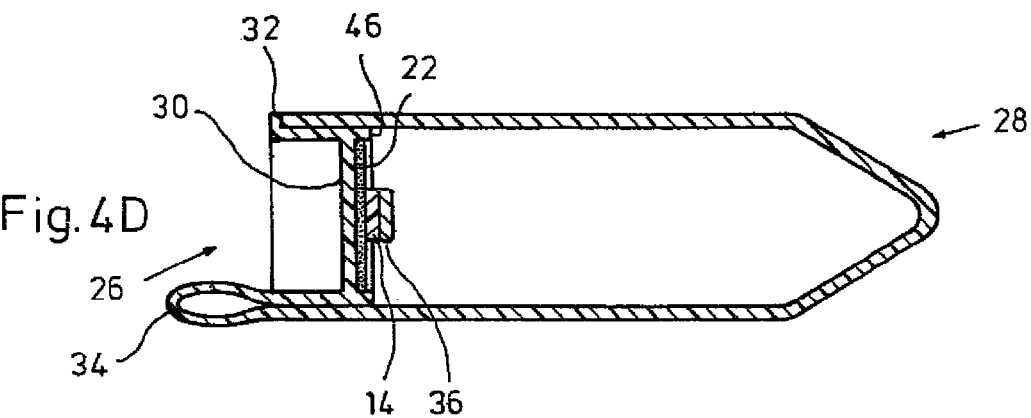

The part 36 of the biological material to be isolated therefore falls onto the seal element 26. The plastic tube 28 is sealed by the seal element 26 (see FIG. 4D). The excised tissue piece 36 is therefore situated in the sterile space of the tube 28. It has therefore been isolated in a highly pure way.

While the invention has been illustrated and described as embodied in a method for isolating a part of a layer of biological material it is not intended to be limited to the details shown since various modifications and desired changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed is:

1. A method for isolating a portion of a layer of biological material, comprising the steps of:
   a) adhering the layer of biological material to one side of a stabilization layer and then applying the stabilization layer to a slide,
   b) providing a substrate and applying a bonding layer to a side of the substrate to be placed into a tube,
   c) bringing the substrate with its bonding layer into contact with the layer of biological material on the stabilization layer;
   d) with a focused laser beam describing a closed or substantially closed curve at the layer of biological material to be isolated where it erodes and excises a portion of only the biological material and the stabilization layer at the described curve; and
   e) separating the substrate with the excised portion of the stabilization layer and the biological material adhering to the substrate.

2. The method as claimed in claim 1, wherein the substrate is configured as a retaining part with a flat bottom, which is acting as a light diffuser; the retaining part having an edge rising above the bottom and further providing a handling device adjoining a side of the edge facing from the bottom.

3. The method as claimed in claim 2, wherein the retaining part acting as a light diffuser is having a bottom provided with a bonding layer on the side opposite from the handling device.

4. The method as claimed in claim 2, wherein the retaining part is integrally connected via a flexible connecting strip to a sealable tube.

5. The method as claimed in claim 2, wherein the edge projects by between 0.1 and 2 mm beyond the bottom on the side where the bonding layer is placed.

6. The method as claimed in claim 2, wherein the retaining part has a bottom with a thickness of at most 2 mm in the vicinity of the light diffuser.

* * * * *